(12) United States Patent
Fu et al.

(10) Patent No.: US 11,937,934 B2
(45) Date of Patent: Mar. 26, 2024

(54) EEG DECODING METHOD BASED ON A NON-NEGATIVE CP DECOMPOSITION MODEL

(71) Applicant: Yanshan University, Qinhuangdao (CN)

(72) Inventors: Rongrong Fu, Qinhuangdao (CN); Yaodong Wang, Qinhuangdao (CN); Shiwei Wang, Qinhuangdao (CN); Bao Yu, Qinhuangdao (CN)

(73) Assignee: YANSHAN UNIVERSITY, Qinhuangdao (CN)

(*) Notice: Subject to any disclaimer, the term of this patent is extended or adjusted under 35 U.S.C. 154(b) by 768 days.

(21) Appl. No.: 17/105,752

(22) Filed: Nov. 27, 2020

(65) Prior Publication Data

US 2021/0161478 A1   Jun. 3, 2021

(30) Foreign Application Priority Data

Nov. 28, 2019 (CN) .......................... 201911194961.X

(51) Int. Cl.
| | |
|---|---|
| *G06N 20/00* | (2019.01) |
| *A61B 5/00* | (2006.01) |
| *A61B 5/369* | (2021.01) |
| *A61B 5/374* | (2021.01) |

(52) U.S. Cl.
CPC .............. *A61B 5/374* (2021.01); *A61B 5/369* (2021.01); *A61B 5/726* (2013.01); *A61B 5/7267* (2013.01); *G06N 20/00* (2019.01)

(58) Field of Classification Search
CPC ......... A61B 5/374; A61B 5/369; A61B 5/726; A61B 5/7267; A61B 5/316; A61B 5/725; G06N 20/00; G06N 20/10; G16H 50/20; G16H 50/70; G06F 18/2411
See application file for complete search history.

(56) References Cited

U.S. PATENT DOCUMENTS

| | | | |
|---|---|---|---|
| 2013/0165812 A1* | 6/2013 | Aksenova ............... | G06F 3/015 600/544 |
| 2016/0242690 A1* | 8/2016 | Principe ................ | A61B 5/316 |
| 2019/0080210 A1* | 3/2019 | Owechko .............. | G06F 18/256 |

* cited by examiner

*Primary Examiner* — Andrey Shostak
(74) *Attorney, Agent, or Firm* — IPRO, PLLC

(57) ABSTRACT

This disclosure provides an EEG decoding method based on a non-negative CP decomposition model. The method extracts time component characteristics of the EEG of the different subjects in the boundary avoidance task, optimizes a characteristic dimension by using a 2-DPCA, and takes classification by using a support vector machine, so that differences of the EEG of subjects in different states can be reflected, and the EEG classification of the single subject has a great accuracy. The time component characteristics of the EEG can be obtained by using the channel components and the frequency components based on the non-negative CP decomposition model and by means of the interaction between the EEG modes. The characteristics of the obtained EEG time components have good separability, and the dimensions of the characteristics are optimized, so that the EEG of left and right hand movements in the boundary avoidance tasks can be effectively decoded.

4 Claims, 2 Drawing Sheets

EEG DECODING METHOD BASED ON A NON-NEGATIVE CP DECOMPOSITION MODEL

TECHNICAL FIELD

The disclosure relates to the field of biological signal processing and pattern recognition, in particular to an EEG decoding method based on a non-negative CP decomposition model.

BACKGROUND

An electroencephalogram (EEG) is a graph, which is obtained by precise electronic instruments amplifying and recording spontaneous biological potential of a brain from the scalp and records spontaneous and rhythmic electrical activities of brain cell groups through electrodes. The EEG has great significance for evaluation of the brain activities, and is an important clinical tool for studying functional state of the brain as well as diagnose and detection of neurological diseases. In the study of the EEG, there is a key step of effectively extracting and identifying characteristic parameters of the specific subjects from the EEG.

During a cognitive neural rehabilitation, a "motion imagination" treatment is usually employed to improve cognitive disorder of stroke patients. Stroke patients rely on their own imagination to stimulate the EEG in a process of the motion imagination, and the motion imagination may activate a motion function of the damaged brain, and repair neural pathways. In recent years, research shows that the EEG is collected in a boundary avoidance task, a participation degree is high, and the EEG carrying characteristics of the subject is more obvious. The extraction of the EEG characteristic parameters is of great significance to the diagnosis of the neurological diseases. In the field of brain-computer interface, the traditional tensor discriminant analysis algorithm generally focuses on extracting frequency component of the EEG of a single motion imagination, constructing a three-order tensor EEG data including channel, frequency and time modes, realizing optimal projection of different dimensions of the EEG data including time, frequency and space modes, thereby improving recognition effect of motion imagination intention, which essentially pertains to enhancement of the EEG characteristics and ignores interaction among the EEG modes.

SUMMARY

An object of the present disclosure is to solve the technical problem of how to extract easily recognizable characteristics of the time components from the EEG of the subject in a boundary avoidance task by utilizing the interaction of the modes of the EEG tensor.

In order to solve the above technical problem, the present disclosure provides an EEG decoding method based on a non-negative CP decomposition model. The method extracts time component characteristics of the EEG of the subject based on a non-negative CP decomposition model, optimizes a characteristic dimension by using a 2-DPCA, and takes classification by using a support vector machine, so that the EEG of left and right hand movements of the subject in the boundary avoidance tasks can be effectively identified.

Compared with the prior art, the present disclosure has following beneficial effects:

The method according to the present disclosure extracts time component characteristics of the EEG of the different subjects in the boundary avoidance task, optimizes a characteristic dimension by using a 2-DPCA, and takes classification by using a support vector machine, so that differences of the EEG of subjects in different states can be reflected, and the EEG classification of the single subject has a great accuracy. The time component characteristics of the EEG can be obtained by using the channel components and the frequency components based on the non-negative CP decomposition model and by means of the interaction between the EEG modes. The characteristics of the obtained EEG time components have good separability, and the dimensions of the characteristics are optimized, so that the EEG of left and right hand movements in the boundary avoidance tasks can be effectively decoded.

DETAILED DESCRIPTION

Hereinafter, embodiments of the present disclosure will be described with reference to the drawings.

Figure 1:
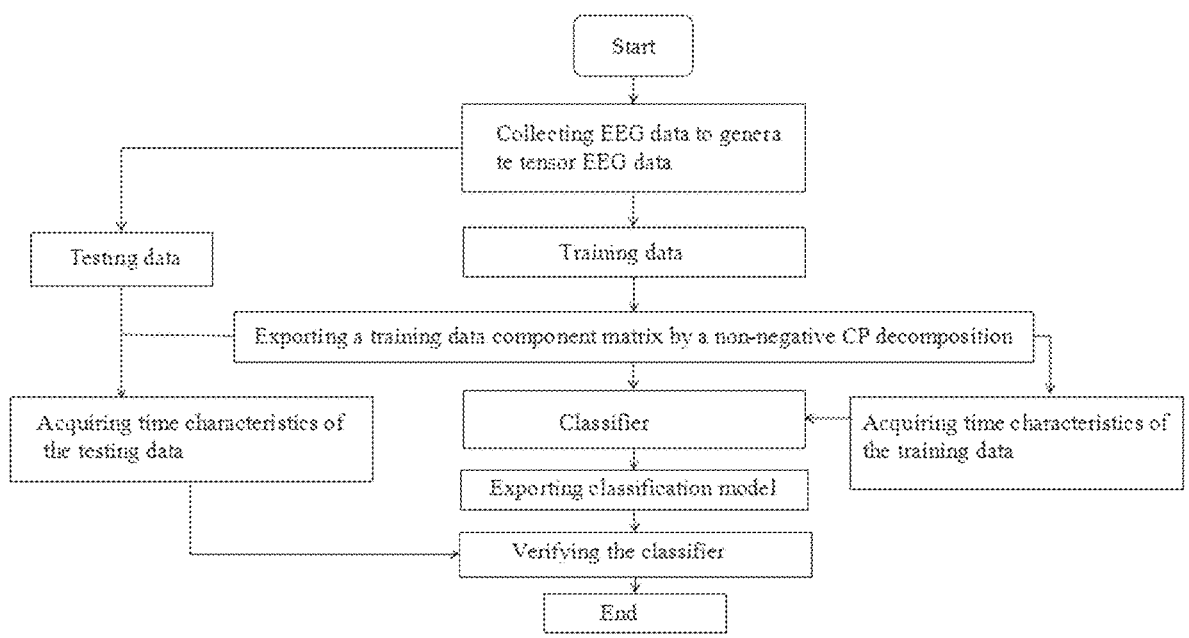
FIG. 1 is an overall flow chart of one implementation of the present disclosure.

An overall flow chart of the EEG decoding method based on the non-negative CP decomposition model is shown in FIG. 1, and the method includes following steps:

step 1, successively truncating EEG data, and filtering by a band-pass filter of 8-13 Hz, and then obtaining frequency components of the EEG by using the complex Morlet wavelet with a bandwidth parameter of $f_b=2$ Hz, constructing a four-order tensor data $X \in i^{c \times f \times t \times s}$, wherein c represents a channel, f represents a frequency, s represents the number of the two types of EEG, in this embodiment, s is 120 including 60 EEG data of the left and right hand motion;

selecting a testing set and a training set by utilizing 5 fold cross-validation, and randomly dividing the EEG data of left and right hands into five groups along a test mode direction, and each group of data is used as the testing set and represented by $X_{test} \in i^{c \times f \times t \times se}$, and the other groups of data are used as the training set and represented by $X_{train} \in i^{c \times f \times t \times sr}$. Firstly, calculating an average value $\overline{X}$ of the training data, and decomposing $\overline{X}$ to obtain three component matrixes $\overline{X} = I \times_1 A \times_2 B \times_3 C + E$, wherein $A \in i^{c \times m}$ represents a channel component matrix, $B \in i^{f \times m}$ represents a frequency component matrix, $C \in i^{t \times m}$ represents a time component matrix, $I \in i^{m \times m \times m}$ represents a unit cubic tensor, $E \in i^{m \times m \times m}$ represents an error tensor, c represents the number of channel, f represents a frequency, s represents the number of the two types of EEG, and m represents a dimension of the unit cubic tensor;

step 2, based on interaction of modes of the EEG, extracting characteristics of the time components from $X_{train}$ and $X_{test}$ by using a component matrix A and a component matrix B, which are expressed as:

$$C_{train} = (X_{train})_{(3)}[(B e A)^T]^{\dagger},\ C_{test} = (X_{test})_{(3)}[(B e A)^T]^{\dagger}$$

in a formula, e represents a Khatri-Rao multiple of a matrix, a superscript † represents pseudo inverse of the matrix, a subscript 3 represents a third mode of the tensor, $C_{train} \in i^{t \times m \times sr}$, $C_{test} \in i^{t \times m \times se}$, t represents a time, and m represents a dimension of the unit cubic tensor I, sr represent the number of training tests, and se represents the number of testing tests;

step 3, optimizing a characteristic dimension of the time component by adopting a 2-DPCA algorithm; and comprising following steps of step 31: calculating a covariance matrix in $C_{train}$:

$$G_t = \frac{1}{sr}\sum_{j=1}^{sr}\{[C_{train,j}^{t\times m} - E(C_{train,j}^{t\times m})]^T[C_{train,j}^{t\times m} - E(C_{train,j}^{t\times m})]\},$$

calculating a characteristic value and a characteristic vector, and taking l characteristic vectors having a cumulative contribution rate of 0.97 of the characteristic value in the characteristic vector to form a column direction projection space $P \in i^{m \times l}$, a column direction projection result is $F_{train,j}=C_{train,j}P$, $F_{test,j}=C_{test,j}P$;

in the formula, $G_t$ is a mean value of a sample covariance matrix in $C_{train}$, $$E(C_{train}) = \frac{1}{sr}\sum_{j=1}^{sr}C_{train,j}^{t\times m}$$

is a mean value of a sample in $C_{train}$, sr represents the number of the training tests, t represents time, and m represents a dimension of a unit cubic tensor I;

step 32, calculating a covariance matrix in $F_{train}$:

$$G_t^* = \frac{1}{sr}\sum_{j=1}^{sr}\{[F_{train,j}^{t\times l} - E(F_{train,j}^{t\times l})][F_{train,j}^{t\times l} - E(F_{train,j}^{t\times l})]^T\};$$

in the formula, $G_t^*$ is a mean value of a sample covariance matrix in $F_{train}$, $$E(F_{train}) = \frac{1}{sr}\sum_{j=1}^{sr}F_{train,j}^{t\times l}$$

is a mean value of the sample in $F_{train}$, sr represents the number of the training tests, t represents time, and m represents a dimension of the unit cubic tensor I;

step 33, evaluating the characteristic value and the characteristic vector of $G_t^*$, and taking d (d<t) characteristic vectors having a cumulative contribution rate of 0.97 of the characteristic value in the characteristic vector to form a row direction projection space $V \in i^{t \times d}$;

step 34, the obtained projection result is expressed as:

$$Q_{train,j}=V^T C_{train,j} P, \quad Q_{test,j}=V^T C_{test,j} P;$$

in the formula, V is a projection space in a row direction, P is a projection space in a column direction, $C_{train,j}$ is a single time component characteristic, $Q_{train,j}$ and $Q_{test,j}$ are the characteristics of the optimized training data and testing data, respectively, and a superscript T represents a transposition of the matrix;

step 4, training the support vector machine with the training data to get a classification model, and then verifying classification performance of the model with the testing data to get the classification accuracy. According to the present disclosure, the EEG characteristics of the left and right hand motion of 10 subjects in the boundary avoidance task are extracted and identified, and the EEG classification accuracy of a single subject is over 90%, and the average EEG recognition accuracy of 10 subjects is 95.42%.

Figure 2:
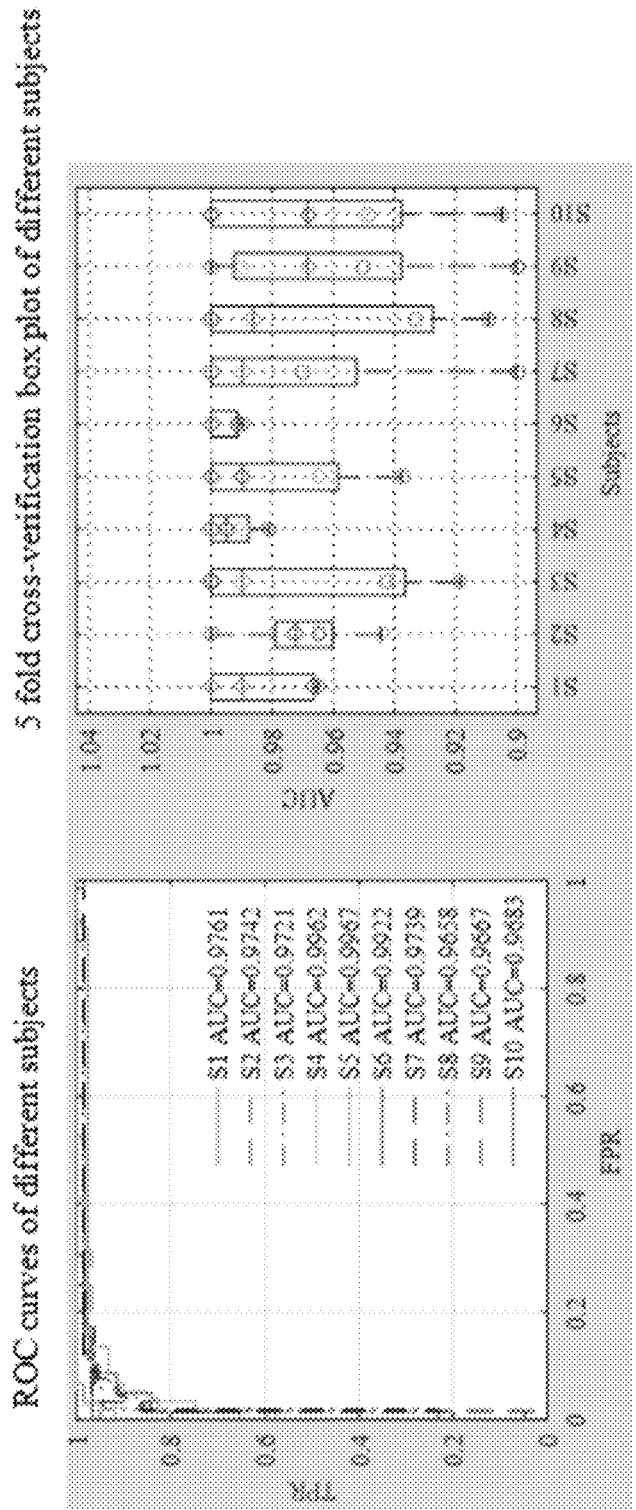
FIG. 2 is ROC graph and cross-validation box plot of EEG classification results of different subjects.

In this embodiment, a ROC curve is used to evaluate the accuracy of classification. ROC curve is a curve drawn with a false positive rate (FPR) as a horizontal axis and a true positive rate (TPR) as a vertical axis. The ROC curves are ought to be above a connecting line of (0, 0) and (1, 1), and an area under the ROC curves is marked as AUC in a value range of [0, 1], in which the greater the value of the AUC, the higher the classification accuracy. FIG. 2 shows the ROC curves and 5 fold cross-validation box plot of S1-S10 subjects. As shown in FIG. 2, the areas under the ROC curves of S1-S10 subjects are larger, over 0.95, which shows that the classification has better accuracy; the AUC of each subject has a higher median value and a smaller range, which indicates that the recognition effect is better. In this embodiment, the classification effects of different classifiers are compared, as shown in the table 1, it turns out that it is better to use SVM classifier for the classification effect of the EEG data. T test is used to verify the classification effect of the SVM classifier. Regarding the EEG data of each subject, the SVM classification results have a row vector discrimination score. The score can be divided into two groups by category labels to obtain two groups of row vectors. Each group represents one class. Whether the two groups of data come from the same distribution is verified by the T test. It is statistically revealed that 95% of the two groups of data may come from different distributions, that is, there is a discrimination (there is 95% possibility to ensure that the classification results are effective).

TABLE 1

Accuracy of Different Classification Methods

| method | Classification Accuracy (%) | | | | | | | | | |
|---|---|---|---|---|---|---|---|---|---|---|
| | S1 | S2 | S3 | S4 | S5 | S6 | S7 | S8 | S9 | S10 |
| SVM | 96.6 | 95.8 | 94.2 | 98.3 | 97.5 | 99.2 | 95.8 | 96.7 | 90.8 | 90.1 |
| Complex tree | 94.9 | 91.7 | 94.2 | 94.2 | 93.3 | 96.6 | 95.8 | 93.3 | 87.5 | 84.2 |
| Linear Discriminant | 94.9 | 91.7 | 93.3 | 96.7 | 94.2 | 98.3 | 95.8 | 95.8 | 88.3 | 91.7 |
| Logistic Regression | 95.8 | 92.5 | 94.2 | 95.8 | 95.0 | 96.6 | 95.0 | 95.0 | 90.8 | 91.7 |
| KNN | 92.4 | 90.0 | 93.3 | 93.3 | 94.2 | 98.3 | 94.2 | 89.2 | 78.3 | 83.3 |

The above-mentioned embodiments only describe the preferred embodiments of the present disclosure, and do not limit the scope of the present disclosure. Various modifications and improvements made by those skilled in the art to the technical solution of the present disclosure without departing from the design spirit of the present disclosure fall in the scope of protection defined by claims of the present disclosure.

What is claimed is:

1. An electroencephalogram (EEG) decoding method based on a non-negative CANDECOMP/PARAFAC (CP) decomposition model, wherein the method comprises the following steps of step 1, acquiring frequency components of EEG data, constructing four-order tensor data including channel, frequency, time and test modes, dividing the four-order tensor data into a training set $\chi_{train}$ and a testing set $\chi_{test}$, calculating an average value $\bar{\chi}$ of the training set $\chi_{train}$, and decomposing $\bar{\chi}$ to obtain three component matrixes $\bar{\chi}=I\times_1 A\times_2 B\times_3 C+E$, wherein $A\in \mathbb{R}^{c\times m}$ represents a channel component matrix, $B\in \mathbb{R}^{f\times m}$ represents a frequency component matrix, $C\in \mathbb{R}^{t\times m}$ represents a time component matrix, $I\in \mathbb{R}^{m\times m\times m}$ represents a unit cubic tensor, $E\in \mathbb{R}^{m\times m\times m}$ represents an error tensor, c represents a channel, f represents a frequency, t represents a time, and m represents a dimension of the unit cubic tensor;

step 2, based on interaction of modes of the tensor, extracting characteristics of the time components from $\chi_{train}$ and $\chi_{test}$ by using a component matrix A and a component matrix B, which are expressed as:

$$C_{train} = (X_{train})_{(3)}[(B\odot A)^T]^{\dagger}, C_{test} = (X_{test})_{(3)}[(B\odot A)^T]^{\dagger}$$

in a formula, $\odot$ represents a Khatri-Rao multiple of a matrix, a superscript $\dagger$ represents pseudo inverse of the matrix, a subscript 3 represents a third mode of the tensor, $C_{train}\in \mathbb{R}^{t\times m\times sr}$, $C_{test}\in \mathbb{R}^{t\times m\times se}$, sr represent the number of training tests, and se represents the number of testing tests;

step 3, optimizing a characteristic dimension of the time component by adopting a two-dimensional principal component analysis (2-DPCA) algorithm; and comprising the following steps of step 31: calculating a covariance matrix in $C_{train}$:

$$G_t = \frac{1}{sr}\sum_{j=1}^{sr}\{[C_{train,j}^{t\times m} - E(C_{train,j}^{t\times m})]^T[C_{train,j}^{t\times m} - E(C_{train,j}^{t\times m})]\},$$

calculating a characteristic value and a characteristic vector, and taking l characteristic vectors having a cumulative contribution rate of 0.97 of the characteristic value in the characteristic vector to form a column direction projection space $P\in \mathbb{R}^{m\times l}$, l<m, a column direction projection result is $F_{train,j}=C_{train,j}P$, $F_{test,j}=C_{test,j}P$;

in the formula, $G_t$ is a mean value of a sample covarianc matrix in $C_{train}$, $$E(C_{train}) = \frac{1}{sr}\sum_{j=1}^{sr}C_{train,j}^{t\times m}$$

is a mean value of a sample in $C_{train}$, sr represents the number of the training tests, t represents time, and m represents a dimension of a unit cubic tensor I;

step 32, calculating a covariance matrix in $F_{train}$:

$$G_t^* = \frac{1}{sr}\sum_{j=1}^{sr}\{[F_{train,j}^{t\times l} - E(F_{train,j}^{t\times l})][F_{train,j}^{t\times l} - E(F_{train,j}^{t\times l})]^T\};$$

in the formula, $G_t^*$ is a mean value of a sample covariance matrix in $F_{train}$, $$E(F_{train}) = \frac{1}{sr}\sum_{j=1}^{sr}F_{train,j}^{t\times l}$$

is a mean value of the sample in $F_{train}$, sr represents the number of the training tests, t represents time, and m represents a dimension of the unit cubic tensor I;

step 33, evaluating the characteristic value and the characteristic vector of $G_t^*$, and taking d characteristic vectors having a cumulative contribution rate of 0.97 of the characteristic value in the characteristic vector to form a row direction projection space $V\in \mathbb{R}^{t\times d}$, d<t;

step 34, the obtained projection result is expressed as:

$$Q_{train,j}=V^T C_{train,j}P, Q_{test,j}=V^T C_{test,j}P;$$

in the formula, V is a projection space in a row direction, P is a projection space in a column direction, $C_{train,j}$ is a single time component characteristic, $Q_{train,j}$ and $Q_{test,j}$ are the characteristics of the optimized training data and testing data, respectively, and a superscript T represents a transposition of the matrix;

step 4, training a support vector machine with the training data to get a classification model, and then verifying classification performance of the model with the testing data to get the classification accuracy;

controlling movement of an external device according to the classification model's decoding result of EEG data of left and right hand movements.

2. The EEG decoding method based on the non-negative CP decomposition model according to claim 1, wherein in step 1, the frequency components of EEG data are obtained by using a complex Morlet wavelet with a bandwidth parameter of $f_b=2$ Hz.

3. The EEG decoding method based on the non-negative CP decomposition model according to claim 2, wherein in step 1, the EEG data is successively truncated, filtered by a band-pass filter of 8-13 Hz, and then the frequency components of the EEG data are obtained by using the complex Morlet wavelet with a bandwidth parameter of $f_b=2$ Hz.

4. The EEG decoding method based on the non-negative CP decomposition model according to claim 1, wherein in step 1, the testing set and training set are selected by 5 fold cross-validation, and the EEG data of left and right hands are randomly divided into five groups along a test mode direction, and each group of data is used as the testing set and represented by $\chi_{test} \in \mathbb{R}^{c \times f \times t \times se}$, and the other groups of data are used as the training set and represented by $\chi_{train} \in \mathbb{R}^{c \times f \times t \times sr}$.

\* \* \* \* \*